US012636140B2

(12) United States Patent
Liu et al.

(10) Patent No.: US 12,636,140 B2
(45) Date of Patent: May 26, 2026

(54) EMBOLIC PROTECTION DEVICE

(71) Applicant: Lifetech Scientific (Shenzhen) Co. Ltd., Shenzhen (CN)

(72) Inventors: Jianyong Liu, Shenzhen (CN); Anning Li, Shenzhen (CN); Yang Ge, Shenzhen (CN); Wancheng Zhu, Shenzhen (CN); Lin Tang, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 118 days.

(21) Appl. No.: 18/290,007

(22) PCT Filed: May 11, 2022

(86) PCT No.: PCT/CN2022/092218
§ 371 (c)(1),
(2) Date: Nov. 8, 2023

(87) PCT Pub. No.: WO2022/237836
PCT Pub. Date: Nov. 17, 2022

(65) Prior Publication Data
US 2024/0252304 A1     Aug. 1, 2024

(30) Foreign Application Priority Data
May 13, 2021     (CN) .......................... 202110521963.6

(51) Int. Cl.
*A61F 2/01*          (2006.01)
*A61F 2/24*          (2006.01)

(52) U.S. Cl.
CPC ............ *A61F 2/013* (2013.01); *A61F 2/0108* (2020.05); *A61F 2/011* (2020.05); *A61F 2/2427* (2013.01);
(Continued)

(58) Field of Classification Search
CPC ........ A61F 2/013; A61F 2/0108; A61F 2/011; A61F 2/2427; A61F 2002/016;
(Continued)

(56) References Cited

U.S. PATENT DOCUMENTS

2013/0103075 A1     4/2013   Wang
2014/0031857 A1     1/2014   Richardson
(Continued)

FOREIGN PATENT DOCUMENTS

CA        2888521 A1 *  4/2014   ............... A61F 2/24
CN     211325886 U  *  8/2020
(Continued)

OTHER PUBLICATIONS

"Hinge", Sep. 4, 2006, Merriam-Webster Dictionary, p. 1 (Year: 2006).*
(Continued)

*Primary Examiner* — Tan-Uyen T Ho
*Assistant Examiner* — Lindsey R. Rivers
(74) *Attorney, Agent, or Firm* — Raymond Sun

(57)          ABSTRACT

An embolic protection device includes a frame, an edge filter screen, and a plurality of supporting rods that are arranged at intervals. Each supporting rod includes a first tail end, a second tail end, and at least one head end that faces a distal end. The first tail end and the second tail end are separately connected to two opposite sides of the frame. The first tail end and the second tail end separately form a first line segment and a second line segment with the head end. The first line segment extends in a direction from the first tail end to the head end and gradually moves away from the frame, and the second line segment extends in a direction from the second tail end to the head end and gradually moves away from the frame.

15 Claims, 12 Drawing Sheets

500

160

110

(52) U.S. Cl.
CPC ................. *A61F 2220/0091* (2013.01); *A61F 2230/0013* (2013.01); *A61F 2250/0098* (2013.01)

(58) Field of Classification Search
CPC ........ A61F 2002/018; A61F 2220/0091; A61F 2230/0013; A61F 2250/0098
See application file for complete search history.

(56) References Cited

U.S. PATENT DOCUMENTS

| | | |
|---|---|---|
| 2021/0220110 A1 | 7/2021 | Ashkenazi et al. |
| 2021/0236258 A1 | 8/2021 | Ashkenazi et al. |

FOREIGN PATENT DOCUMENTS

| | | | | |
|---|---|---|---|---|
| EP | 3 400 901 A1 | 11/2018 | | |
| EP | 3 145 445 B1 | 3/2019 | | |
| WO | WO-2015177322 A1 * | 11/2015 | .......... | A61M 25/007 |
| WO | WO2021104063 | 6/2021 | | |

OTHER PUBLICATIONS

International Search Report dated Aug. 16, 2022 for corresponding PCT Application No. PCT/CN2022/092218.
Office action dated Apr. 2, 2025 in corresponding European Appl. No. 22 80 6798.
Office action dated Jun. 25, 2025 in corresponding China Application No. 202280003954.0.
Second Office action dated Oct. 18, 2025 in corresponding China Appl. No. 202280003954.0, and translation.

* cited by examiner

100

500

132

160

500

160

110

400          500          300

E

111

142

110

160

140

142   141

110

F

F

G 111
111

142

110

160

140
142    141

110

K

K

700

J

142

110          170

171          142

172

800

S

EMBOLIC PROTECTION DEVICE

TECHNICAL FIELD

The embodiments relate to the technical field of interventional medical devices, and in particular to an embolic protection device.

BACKGROUND

Cerebral embolism refers to various emboli in the blood (such as mural thrombi in the heart, atherosclerotic plaque, fat, tumor cells, fibrocartilage, or air), which enter the narrow and curved cerebral artery with blood flow and obstruct the blood vessel, causing ischemic necrosis of the brain tissue in the blood supply area of the artery and resulting in focal neurological deficit when the collateral circulation cannot compensate. Cerebral embolism often occurs in the internal carotid artery system, and relatively rarely in the vertebral-basilar artery system. Cerebral embolism accounts for about 15%-20% of ischemic stroke. About 75% of cardiogenic emboli embolize in the brain, and common heart diseases leading to cerebral embolism include atrial fibrillation, heart valve disease, infective endocarditis, and cardiac myxoma. With the improvement in medical treatment, increasing problems with cardiac and vascular surgery can be solved through endovascular procedures. Stent implantation and valve replacement are endovascular procedures that have developed rapidly in recent years. Among them, the valve replacement is mainly transcatheter aortic valve implantation (TAVI), which is designed to deliver an interventional catheter through the femoral artery to deliver the prosthetic heart valve to the aortic valve area to open, so as to complete the implantation of the prosthetic valve and restore the valve function. The procedure does not require thoracotomy, bringing less trauma and faster postoperative recovery. The valve replacement in combination with an embolic protection device may effectively prevent emboli from entering the cranium and causing obstruction, thus further reducing the risk.

At present, effective filtration of emboli is required at all of three branches of the arch of the aorta to minimize the risk of stroke, according to clinical studies. Most of existing embolic protection devices include a structure of a nitinol frame with a filter membrane to block off the three branches of the arch of the aorta. For a protection device of such a structure, the filter membrane is usually supported by a sheath-core which curves at the arch to filter thrombi at the three branches. There are also embolic protection devices that typically attach a cut and pre-curved supporting screen to inner walls at the three branches to effect filtration. However, in the clinical application of these protection devices, the filter membrane or filter screen cannot attach well to the walls of the arch of the aorta at the three branches, resulting in some emboli still entering the branches of the arch of the aorta, which has potential safety hazards.

SUMMARY

In view of the above, a new embolic protection device is desired that addresses the problem that the filter membranes or filter screens of existing embolic protection devices cannot attach well to the three branches of the arch of the aorta.

An embolic protection device is provided, including a frame and a filter screen covering the frame, where the embolic protection device further includes a plurality of supporting rods that are arranged at intervals in an axial direction thereof, each supporting rod includes a first tail end, a second tail end, and at least one head end that faces a distal end, the first tail end and the second tail end are separately connected to two opposite sides of the frame, a first line segment is formed between the first tail end and the head end, and a second line segment is formed between the second tail end and the head end, the first line segment extends in a direction from the first tail end to the head end and gradually moves away from the frame, and the second line segment extends in a direction from the second tail end to the head end and gradually moves away from the frame, such that the plurality of supporting rods support the filter screen, which covers the plurality of supporting rods, in a direction facing away from the frame.

In one embodiment, the vertical distance from a highest point on the supporting rods to a horizontal plane is greater than or equal to 0 mm and less than or equal to 30 mm when the embolic protection device is placed on the horizontal plane.

In one embodiment, the vertical distance between a vertical projection point of the head end to the horizontal plane and a line connecting vertical projection points of the first tail end and the second tail end to the horizontal plane is greater than or equal to 20 mm and less than or equal to 120 mm.

In one embodiment, the shortest distance between the first tail end and the second tail end ranges from 20 mm to 100 mm.

In one embodiment, at least one of the head ends curves and extends towards the distal end and towards the frame.

In one embodiment, at least one of the head ends is provided with a damage-prevention element.

In one embodiment, at least one sliding-restraint ring is provided on the embolic protection device.

In one embodiment, the sliding-restraint ring is arranged on the frame of the embolic protection device or on at least one of the head ends of at least one supporting rod.

In one embodiment, the embolic protection device is provided with at least one imaging member at a proximal and/or distal end thereof.

In one embodiment, the embolic protection device further includes a connecting member connected to a proximal end of the frame.

In one embodiment, the connecting member is rotatably connected to the frame.

In one embodiment, at least one connecting hole is arranged on the proximal end of the frame, and a distal end of the connecting member is fixed to the connecting member through the connecting hole, such that the connecting member is rotatably connected to the frame.

In one embodiment, the connecting member is connected to the frame by a universal ball.

In one embodiment, the connecting member is connected to the frame by a hinge.

An embolic protection system is further provided, including an elongate sheath-core and the embolic protection device of any one of the embodiments above.

In one embodiment, at least one sliding-restraint ring is provided on the embolic protection device, one end of the embolic protection device is fixed to the sheath-core and the other end is axially movable along the sheath-core through the sliding-restraint ring.

In the embolic protection device and the embolic protection system thereof described above, the embolic protection device includes a plurality of supporting rods that are arranged at intervals in an axial direction thereof. A first tail end and a second tail end of each supporting rod are separately connected to two opposite sides of the frame. A first line segment formed between the first tail end and the head end and a second line segment formed between the second tail end and the head end on each supporting rod separately extend in directions from corresponding tail ends to the head end and gradually move away from the frame. Such a structural design enables the supporting rods to extend upwardly towards the distal end and away from the frame, and the head ends of the supporting rods are suspended, so as to support the filter screen, which covers the supporting rods, upward in a direction facing away from the frame. Therefore, the filter screen can be attached to three branches of the arch of the aorta without the aid of a sheath-core. In addition, during practical application, the frame and the supporting rods can interact with and reinforce each other, which can not only facilitate a more stable fixation of the frame at the arch of the aorta, but also facilitate the supporting rods to provide a larger upward supporting force for the filter screen, thereby better attaching the filter screen to the upper wall tissue of the arch of the aorta.

DETAILED DESCRIPTION OF THE EMBODIMENTS

In order that the objects, technical schemes, and advantages of the embodiments become clearer, the embodiments will be further illustrated in detail below with reference to the drawings and embodiments. It is to be understood that the particular embodiments described herein are illustrative only and are not intended to be limiting.

It is to be noted that in the field of interventional medical devices, an end of a medical device implanted in a human body or an animal body which is close to the operator is generally called a "proximal end", and an end which is far away from the operator is called a "distal end", and therefore a "proximal end" and a "distal end" of any part of a medical device may be defined in accordance with this principle. An "axial" direction generally refers to a length direction of a medical device as it is delivered, and a "radial" direction generally refers to a direction of the medical device perpendicular to the "axial" direction thereof, and therefore an "axial" direction and a "radial" direction of any part of a medical device may be defined in accordance with this principle.

Hereinafter, the technical schemes of the embodiments will be described in further detail with reference to specific embodiments.

Embodiment 1

In Embodiment 1, an embolic protection device is provided for use in valve replacement surgery, for example, to prevent, at the position of the arch of the aorta, particles such as thrombi or clots in the blood flow from entering the brain through any of three branches of the arch of the aorta which may result in cerebral embolism. In addition, the device can be used in thoracotomy to filter blood, or implanted into blood vessels to filter particles or particulates such as thrombi or calcifications.

Figure 1:
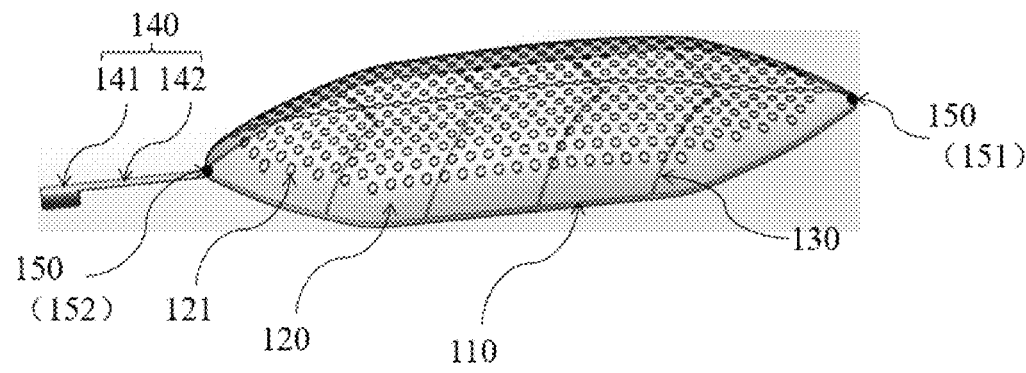
FIG. 1 is an overall structural diagram of an embolic protection device of Embodiment 1.
Figure 2:
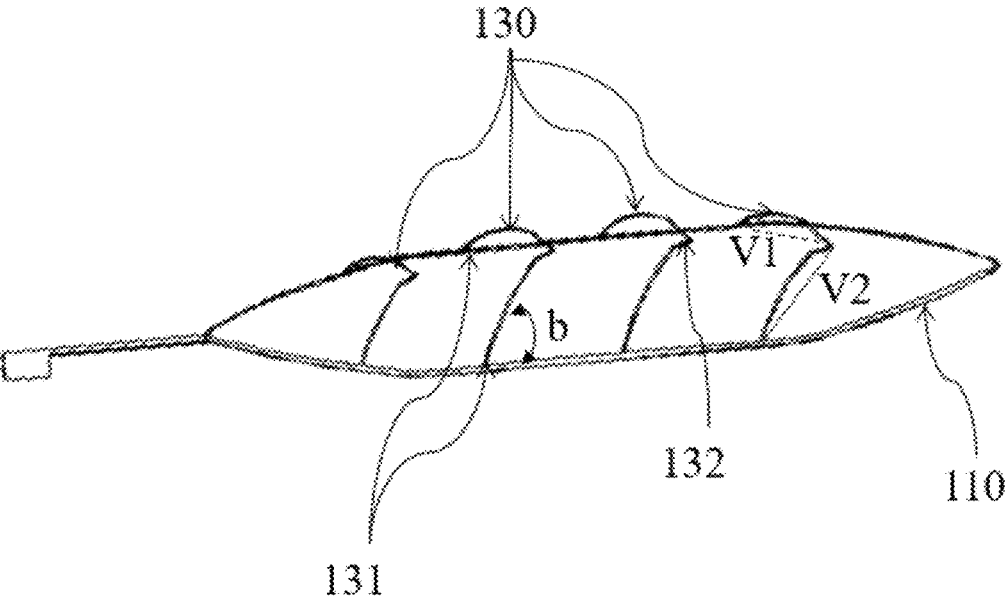
FIG. 2 is a structural diagram of the embolic protection device of FIG. 1 without covering with a filter screen.

Referring to FIGS. 1 and 2, the embolic protection device 100 includes a frame 110 and a filter screen 120 covering the frame 110, and four supporting rods 130 that are arranged at intervals in an axial direction of the embolic protection device 100. Each supporting rod 130 is V-shaped and includes a first tail end 131, a second tail end 131, and a head end 132 that faces a distal end. The first tail end 131 and the second tail end 131 are fixedly connected to two opposite sides of the frame 110, separately. A virtual first line segment V1 is formed between the first tail end 131 and the head end 132, and a virtual second line segment V2 is formed between the second tail end 131 and the head end 132. The first line segment V1 extends in a direction from the first tail end 131 to the head end 132 and gradually moves away from the frame 110, and the second line segment V2 extends in a direction from the second tail end 131 to the head end 132 and gradually moves away from the frame 110, i.e., at least part of each supporting rod 130 extends from its corresponding first tail end 131 and second tail end 131 separately towards the head end 132 corresponding thereto and gradually moves away from the frame 110, so as to support the filter screen 120, which covers the four supporting rods 130, upward in a direction facing away from the frame 110. In some embodiments, a part of the supporting rods 130 may be selected to support the filter screen 120 upward in a direction facing away from the frame 110, and the other part of the supporting rods 130 may have other shapes and other functions.

The frame 110 is a closed ring frame in the embolic protection device 100. The frame 110 is shaped like an oval or like a leaf that is hollow inside, etc. The frame 110 may be made of an alloy or polymer material with shape memory properties, such as nitinol, cobalt-chromium alloy, TPU (thermoplastic polyurethanes), PTFE (poly tetra fluoroethylene), and PE (polyethylene). The plane bounded by the frame 110 may be parallel to the horizontal plane or may be an arcuate plane that conforms to the shape of the arch of the aorta.

The filter screen 120 is a membrane made of a polymer material such as PTFE, TPU, or PET (polyethylene terephthalate), or made of braided wires with shape memory properties. The filter screen 120 may have a thickness ranging from 10 microns to 55 microns, and the membrane has a plurality of pores 121 for filtration, each having a pore size ranging from 25 microns to 300 microns. The filter screen 120 is shaped and sized similar to, or matching with, the frame 110, so long as the filter screen 120 can completely cover the frame 110 and the edge of the filter screen 120 can be fixedly connected to the frame 110. An edge portion of the filter screen 120 is fixedly connected to the frame 110 through a process such as glue, radiofrequency, laser welding, and stitching. The filter screen 120 is capable of filtering large particles such as large thrombi or clots, as well as small particles, such as small lumps or clots.

The supporting rods 130 may be made of the same material as the frame 110. The supporting rods 130 may be separately manufactured and then fixed on the frame 110, or may be made of the same sheet material as the frame 110 by cutting and heat setting. In the axial direction of the embolic protection device 100, a minimum spacing between head ends 132 of two adjacent supporting rods 130 ranges from 5 mm to 100 mm. The first tail end 131 and the second tail end 131 on the same supporting rod 130 can be symmetrical about a central axis of the frame 110, which can not only facilitate a greater radial support force and anchoring stability of the frame 110, but also attach the filter screen 120 to the upper wall of the arch of the aorta to a maximum extent. In other implementations, the first tail end 131 and the second tail end 131 of the same supporting rod 130 may be asymmetrical about the central axis of the frame 110. The head end 132 of each supporting rod 130 is suspended away from the frame 110, and a first portion between the first tail end 131 and the head end 132 and a second portion between the second tail end 131 and the head end 132 of each supporting rod 130 gradually support the filter screen 120, which covers the supporting rods 130, upward in a direction facing away from the frame 110, such that the portion of the filter screen 120 can be stably attached to the upper wall of the arch of the aorta without the aid of a sheath-core for support. In other implementations, the number of supporting rods 130 may be varied, such as three or five, as desired.

Figure 3:
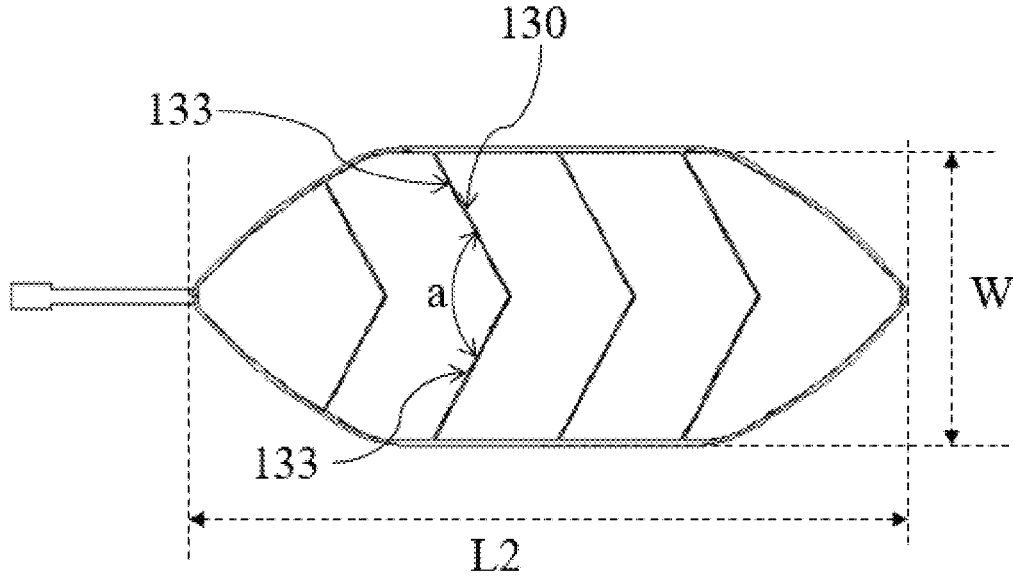
FIG. 3 is a top view of the structure shown in FIG. 2.

As shown in FIG. 3, an included angle a between two rod portions 133 forming a V-shaped rod 130 ranges from 10 degrees to 145 degrees. If the included angle a is less than 10 degrees, the supporting rods 130 may not provide sufficient spreading force to the frame 110 in the expansion of the embolic protection device 100, such that the frame 110 may not be well anchored to the inner wall of the arch of the aorta. If the included angle a is greater than 145 degrees, the embolic protection device 100 is less flexible in the radial direction and may damage blood vessels. In this embodiment, the included angle a between the two rod portions 133 of each supporting rod 130 is 135 degrees.

Figure 4:
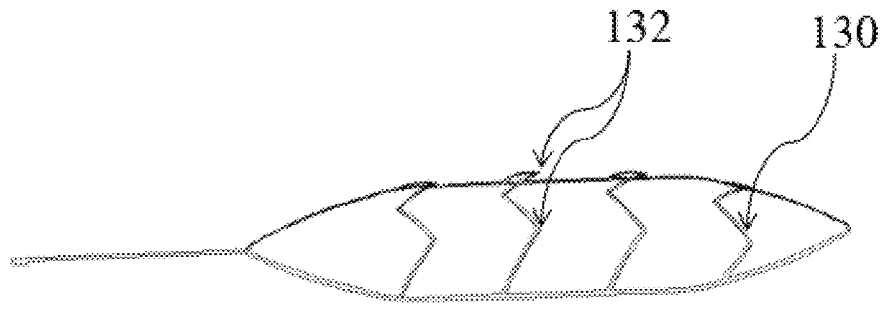
FIG. 4 is another structural diagram of the embolic protection device of Embodiment 1 without covering with a filter screen.
Figure 5:
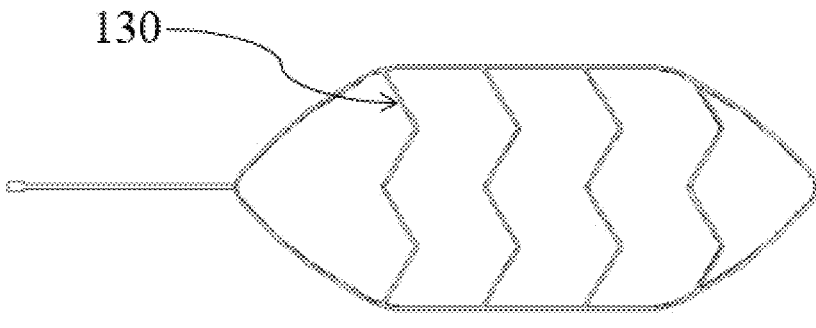
FIG. 5 is a top view of the structure shown in FIG. 4.

In other implementations, the supporting rods 130 may be U-shaped rods as well. Alternatively, the supporting rods 130 may each be formed by two or more V-shaped rods and/or U-shaped rods in series, such as W-shaped rods 130 formed by two V-shaped rods as shown in FIGS. 4 and 5. Further, the supporting rods 130 may be zigzag-shaped rods formed by more than two V-shaped rods, or wave-shaped rods formed by more than two U-shaped rods, in which case the supporting rods 130 each have two or more head ends 132, such that the supporting rods 130 attach the filter screen 120 to the upper wall of the arch of the aorta at various points, and the supporting rods 130 have better deployment strength, enabling the frame 110 to be better anchored in the arch of the aorta. For a supporting rod 130 having two or more head ends 132, a first line segment V1 may be a virtual line segment formed between a first tail end 131 of the supporting rod 130 and any one of the head ends 132 on the supporting rod 130, and a second line segment V2 may be another virtual line segment formed between a second tail end 131 of the supporting rod 130 and any one of the head ends 132 on the supporting rod 130.

The four supporting rods 130 in FIG. 1 vary in length. Specifically, the length increases from the proximal end to the distal end of the embolic protection device 100. The four supporting rods 130 all curve towards the distal end, and the degree of curvature may vary as long as they cooperate to ensure that the supported filter screen 120 is fully attached to the upper wall of the three branches of the arch of the aorta. As one implementation and as shown in FIG. 2, a minimum included angle b between the supporting rods 130 and the frame 110 is greater than or equal to 10 degrees and less than or equal to 80 degrees.

Figure 6:
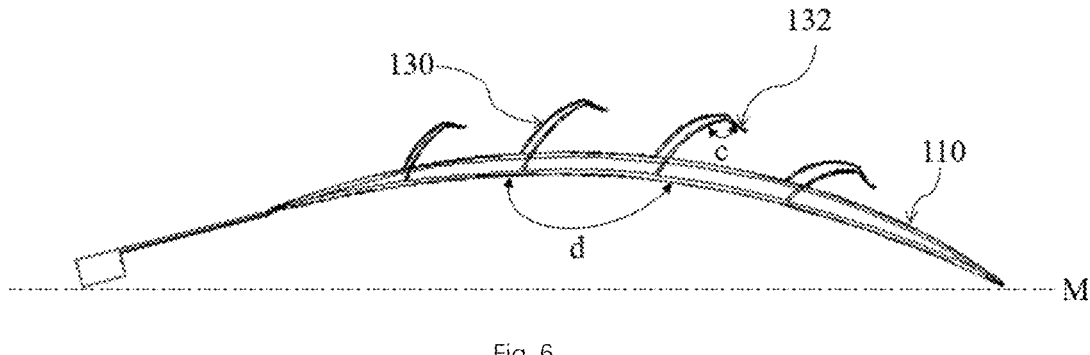
FIG. 6 is another structural diagram of the embolic protection device of Embodiment 1 without covering with a filter screen.

In this embodiment, the four head ends 132 on the embolic protection device 100 are each curved towards the distal end and slightly downward towards the frame 110, thereby preventing the distal end portions of the head ends 132 from puncturing the filter screen 120 while entering and leaving the sheath 400, or puncturing the upper wall tissue of the arch of the aorta during deployment. In order to better avoid this problem, the head end 132 of each supporting rod 130 may be further rounded off. In other implementations, at least one of the head ends 132 is provided with a damage-prevention element, such as a ball formed by hot melting the head end 132, or silicone wrapped around the head end 132, to prevent the head end 132 from puncturing the filter screen 120. In other implementations, the head end 132 of each supporting rod 130 may extend towards the distal end while extending slightly upwards away from the frame 110. In this case, the head end 132 may be rounded off as described above or provided with the damage-prevention element as described above, with the head end 132 being a highest point on the supporting rod 130 where it is located. In other implementations and as shown in FIG. 6, all of the head ends 132 curve and extend towards the distal end and downward towards the frame 110 for a short distance, the curvature c of the head ends 132 curving downward ranging from R2 to R30, such that the portions of the supporting rods 130 in contact with the filter screen 120 have no tips, and the supporting rods 130 are in smooth contact with the filter screen 120, thereby preventing the head ends 132 from puncturing the filter screen 120. In embodiments where a supporting rod 130 includes two or more head ends 132, one or more of the head ends 132 of the supporting rods 130 may be used in the manner described above to prevent the head ends 132 from puncturing the filter screen 120, which will not be described in detail herein.

Figure 7:
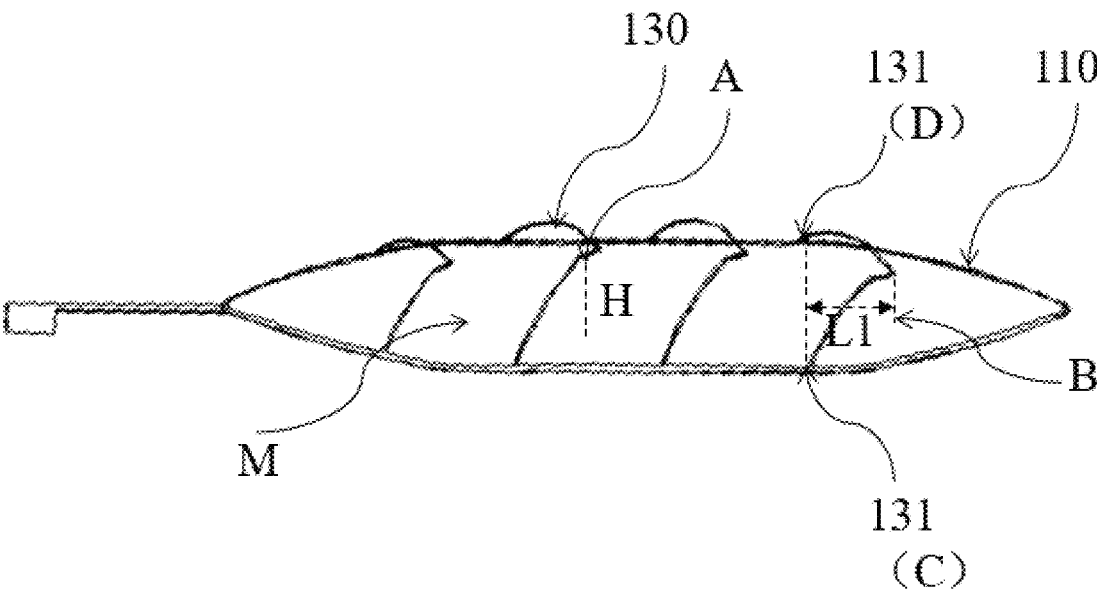
FIG. 7 is a structural diagram of the structure shown in FIG. 2 being placed on a horizontal plane.

As shown in FIG. 7, when the embolic protection device 100 shown in FIG. 2 is placed on a horizontal plane M, the frame 110 is in contact with the horizontal plane M. In one supporting rod 130, for example, a vertical distance H from a highest point on the supporting rod 130 to the horizontal plane M is greater than or equal to 0 mm and less than or equal to 30 mm, e.g., 0 mm, 10 mm, 20 mm, or 30 mm. In this embodiment, the head end 132 is not the highest point on the supporting rod 130 as the head end 132 is slightly curved downward. If the vertical distance H from the highest point on the supporting rod 130 to the horizontal plane M is greater than 30 mm, a height difference between the first tail end 131 or the second tail end 131 of the supporting rod 130 and the head end 132 is too large to facilitate the attachment of the supporting rod 130 to the filter screen 120 as a whole, thereby affecting the sealing of the filter screen 120 at the three branches. If the vertical distance H from the highest point on the supporting rod 130 to the horizontal plane M is less than 0 mm, the supporting height of the supporting rod 130 is limited, which is not conducive to the attachment of the filter screen 120 to the upper wall of the arch of the aorta. Assuming that the point A on the supporting rod 130 in FIG. 7 is the highest point, the vertical distance from the point A to the horizontal plane M is H.

The vertical distance L1 between a vertical projection point B of the head end 132 of the supporting rod 130 to the horizontal plane M and a line CD connecting a vertical projection point C of the first tail end 131 of the supporting rod 130 to the horizontal plane M and a vertical projection point D of the second tail end 131 to the horizontal plane M is greater than or equal to 20 mm and less than or equal to 120 mm, e.g., 30 mm. The shortest distance between the first tail end 131 and the second tail end 131 of the supporting rod 130, i.e., the length of the straight line CD, ranges from 20 mm to 100 mm. For example, the shortest distance between the first tail end 131 and the second tail end 131 may be 50 mm.

Figure 8:
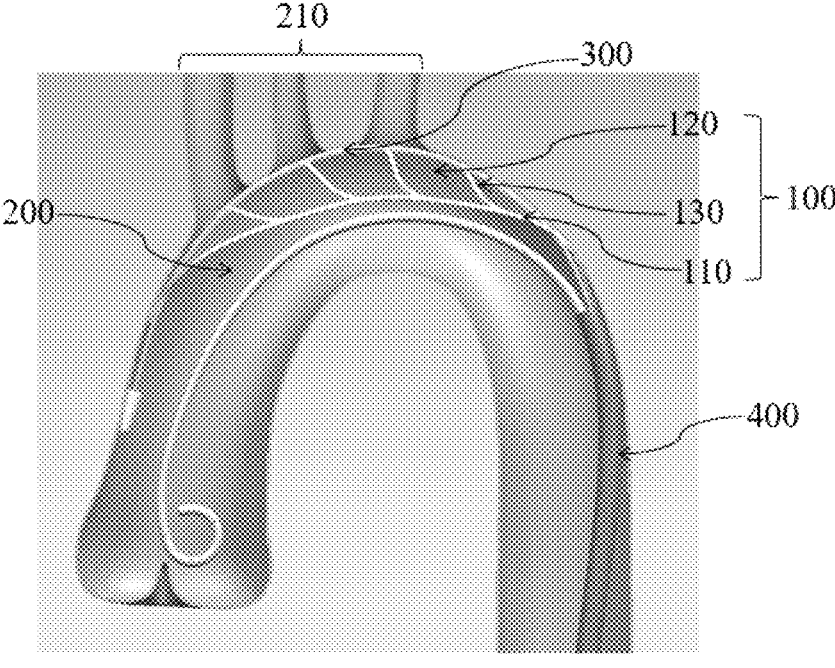
FIG. 8 is a schematic diagram of the embolic protection device of FIG. 1 being implanted at an arch of the aorta.

As shown in FIG. 8, after the embolic protection device 100 is implanted into the arch of the aorta 200, the plurality of supporting rods 130 cooperate with each other not only to fully attach the filter screen 120 at the three branches 210 of the arch of the aorta 200, but also to interact with the frame 110 compressed by the inner wall of the arch of the aorta 200. On one hand, the frame 110 transmits a part of the compressive force to the supporting rods 130, such that the supporting rods 130 further support the filter screen 120 upwardly, so as to further attach the filter screen 120 to the upper wall at the three branches 210 of the arch of the aorta 200. On the other hand, the supporting rods 130 react to the frame 110 to outwardly spread two sides of the frame 110 connected to the supporting rods 130, such that the frame 110 can be stably anchored to the inner wall of the arch of the aorta 200.

In this embodiment, the frame 110 is substantially fully attached to the horizontal plane M when the embolic protection device 100 is placed on the horizontal plane M. In another implementation and as shown in FIG. 6, when the embolic protection device 100 is placed on the horizontal plane M, only the distal portion of the frame 110 is in contact with the horizontal plane M, while the middle portion of the frame 110 is bowed upwardly, i.e., the frame 110 is curved with respect to the horizontal plane M, and the curvature d of the curve ranges from R20 to R200, such that the curved frame 110 can facilitate the supporting rods 130 and the filter screen 120 to be better attached to the upper wall of the arch of the aorta 200 after the embolic protection device 100 is released.

When the embolic protection device 100 is placed on the horizontal plane M, as shown in FIG. 3, an axial length L2 of the frame 110 ranges from 50 mm to 150 mm. In the axial direction of the frame 110, the width of the frame 110 may vary in different regions, and the maximum width W may range from 30 mm to 100 mm, thus covering the three branches 210 of the arch of the aorta 200 in most anatomical structures, achieving effective embolic protection.

In this embodiment, the filter screen 120 only covers the supporting rods 130 without being fixedly connected thereto. In other implementations, a portion of each of the supporting rods 130 may be partially fixed to the filter screen 120 by glue or stitching. In a case where a supporting rod 130 includes two or more head ends 132, it is also possible to prevent the head ends 132 from hinging in the process of entering sheath.

As shown in FIG. 1, a proximal end portion of the frame 110 is provided with a connecting member 140 connected to a distal end of a sheath-core 300. The connecting member 140 may be made of nitinol, a proximal section 141 of the connecting member 140 is tubular that is hollow inside, a distal section 142 is rod-shaped, and a distal end portion of the proximal section 141 is directly connected to the proximal end portion of the distal section 142. The proximal section 141 of the connecting member 140 allows the sheath-core 300 to extend towards the distal end for a further distance after the distal end of the sheath-core 300 enters the proximal end and leaves the distal end of the proximal section 141, until the distal end portion of the sheath-core 300 is closer to the distal end than the distal end portion of the embolic protection device 100. After implantation into the arch of the aorta 200, the distal section 142 may abut against the sheath-core 300. In clinical application, the embolic protection device 100 may be fixedly connected to the distal end of the sheath-core 300 via the proximal section 141 of the connecting member 140. In other implementations, the embolic protection device 100 may also be fixedly connected to the sheath-core 300 via the frame 110 or the supporting rods 130.

In order to facilitate visualization of the surgical procedure through a digital subtraction angiography (DSA) device, at least two imaging members 150 may be provided on the embolic protection device 100, as shown in FIG. 1. The imaging members 150 may be made of a material developable in a DSA device, such as gold, platinum, platinum iridium alloy, or other materials with strong developability. The specific structure, shape, etc., of the imaging members 150 is not limited as long as it can be fixed in place on the embolic protection device 100. Specifically, a first imaging member 151 may be arranged at the distal end portion of the embolic protection device 100, and a second imaging member 152 may be arranged at the proximal end portion of the embolic protection device 100. In other embodiments, additional imaging members 150 may be provided at other locations on the embolic protection device 100, such as on the head ends 132 of the supporting rods 130 in the central region of the embolic protection device 100, so as to assist in determining whether the filter screen 120 on the embolic protection device 100 is effectively attached to the upper wall of the arch of the aorta 200.

This embodiment also provides an embolic protection system including the embolic protection device 100 and the sheath-core 300 described above, the embolic protection system further including a sheath 400 for compressing and delivering the embolic protection device 100 described above. The embolic protection device 100 described above has superelasticity and shape memory properties. After being fixed to the distal end of the sheath-core 300, the embolic protection device 100 is compressed as being drawn into the sheath 400 by the sheath-core 300, so as to facilitate delivery of the embolic protection device 100 into the body via the sheath 400. After extending from the sheath 400, the embolic protection device 100 self-expands under the action of shape memory properties to assume a deployed state as shown in FIG. 1. The deployed shape of the embolic protection device 100 released at the arch of the aorta 200 is generally the same as the naturally deployed state thereof as shown in FIG. 1 and may vary slightly depending on a specific implantation into the arch of the aorta 200. The above description of the embolic protection device 100, without specific indication, describes features in the deployed state.

Prior to a surgery, one end of the embolic protection device 100 needs to be fixed in place on the distal end of the sheath-core 300. The proximal end of the embolic protection device 100 can be fixed on the sheath-core 300 while the distal end is not fixed. Alternatively, the distal end of the embolic protection device 100 can be fixed on the sheath-core 300 while the proximal end is not fixed. The fixation of the proximal end portion of the embolic protection device 100 to the sheath-core 300, for example, is described in detail below. The proximal end of the sheath-core 300 enters the distal end of the sheath 400 and leaves the proximal end of the sheath 400 along a luminal path of the sheath 400 until the embolic protection device 100 is drawn into the distal lumen of the sheath 400 such that the embolic protection device 100 is radially compressed, axially elongated, and housed within the distal end of the sheath 400 in a compressed state.

During the surgery, a puncture is performed at a femoral artery at one side of a human body or an animal body, and then a guidewire is fed to establish a delivery path in the body. After the guide wire reaches a predetermined position, the sheath 400 housing the embolic protection device 100 is delivered along the guidewire path to a region where the arch of the aorta 200 is located. At this time, with the aid of a DSA device, the relative positions of the embolic protection device 100 and the three branches 210 of the arch of the aorta 200 are determined based on positions of the plurality of imaging members 150 arranged on the embolic protection device 100. When it is observed through the DSA device that the first imaging member 151 and the second imaging member 152 on the embolic protection device 100 are located separately at two ends of the region of the three branches 210 of the arch of the aorta 200, the sheath-core 300 is maintained stationary, and the sheath 400 is slowly withdrawn, so as to gradually release the embolic protection device 100 from the sheath 400, until the embolic protection device 100 completely extends from the distal end of the sheath 400 and self-expands and deploys to cover the three branches 210 of the arch of the aorta 200. Then a pigtail catheter is configured for entering the femoral artery at the side and pass through the arch of the aorta 200 to reach the position of a calcified aortic valve for radiography. The aortic valve replacement sheath 400 is introduced into the body through a puncture at a femoral artery at an opposite side until reaching the aortic valve for valve replacement. During the replacement, particles or particulates such as detached calcified tissues and emboli move with the blood flow towards the arch of the aorta 200. Since the embolic protection device 100 has established a strict filtering mechanism at the openings of the three branches 210 of the arch of the aorta 200, floats such as emboli and calcified tissues are deflected by the embolic protection device 100 to the descending aorta, thereby preventing these floats from flowing to the brain through the three branches 210. After the completion of the aortic valve replacement, the aortic valve replacement sheath 400 is withdrawn. The sheath 400 is then advanced towards a distal end to compress and house the embolic protection device 100 within the distal end of the sheath 400, and then the embolic protection device 100 is withdrawn from the body along with the sheath 400, etc., to complete the procedure.

Embodiment 2

In Embodiment 2, another embolic protection device and an embolic protection system thereof are provided. The embolic protection device 500 of Embodiment 2 is generally similar to the embolic protection device 100 of Embodiment 1, as are the definitions and features of the virtual first line segment V1 and the virtual second line segment V2, and the surgical procedures. The main difference between the two devices lies in that the embolic protection device 500 of Embodiment 2 is provided with at least one sliding-restraint ring 160 which may be arranged on the frame 110 or on at least one head end 132 of the supporting rods 130. In the embolic protection system of Embodiment 2, the distal end of the sheath-core 300 passes through one or more sliding-restraint rings 160 on the embolic protection device 500, such that when the embolic protection device 500 is compressed by the arch of the aorta 200, the sliding-restraint rings 160 can move axially along the sheath-core 300, such that the whole embolic protection device 500 can curve and deform adaptively to be better attached to the upper wall of the arch of the aorta 200, achieving a greater embolic protection effect, while preventing the embolic protection device 500 from shifting with respect to the sheath-core 300 which may result in ineffective filtration of thrombi, etc.

Figure 9:
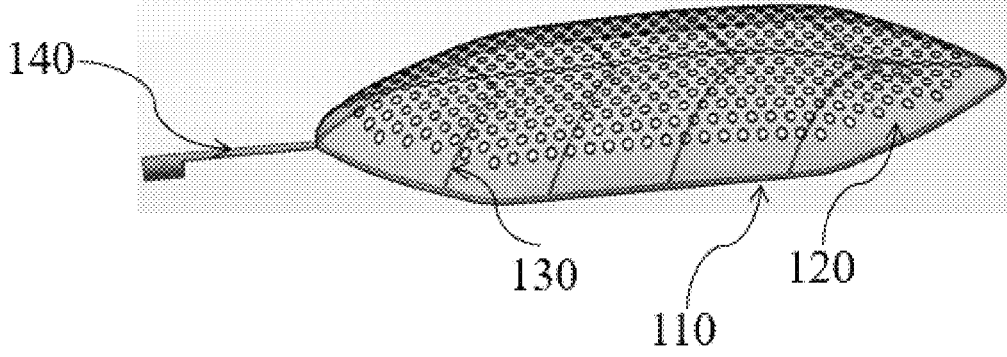
FIG. 9 is an overall structural diagram of an embolic protection device of Embodiment 2.
Figure 10:
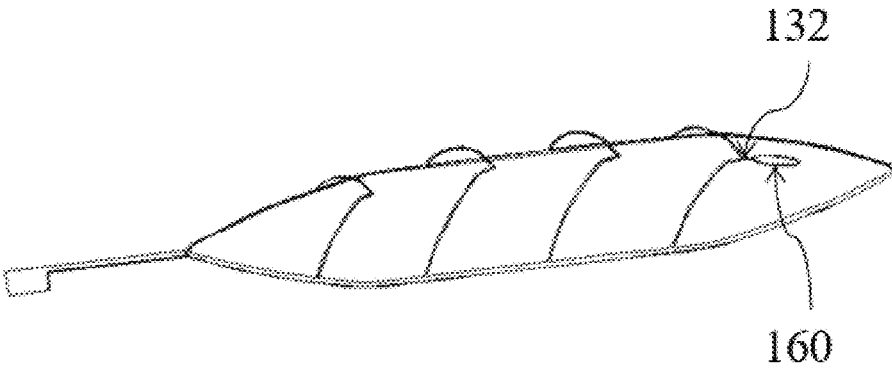
FIG. 10 is a structural diagram of the embolic protection device of FIG. 9 without covering with a filter screen.
Figure 11:
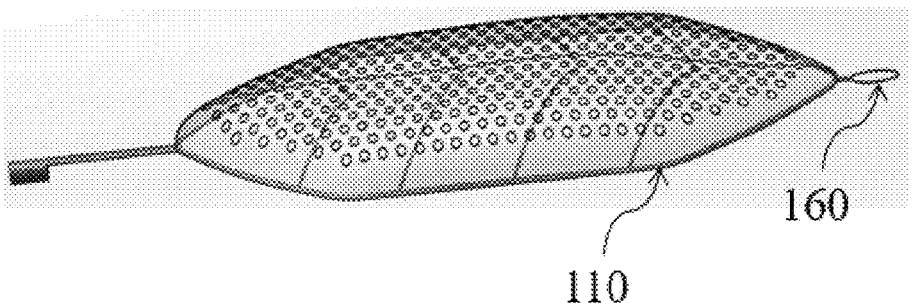
FIG. 11 is another structural diagram of an embolic protection device of Embodiment 2.
Figure 12:
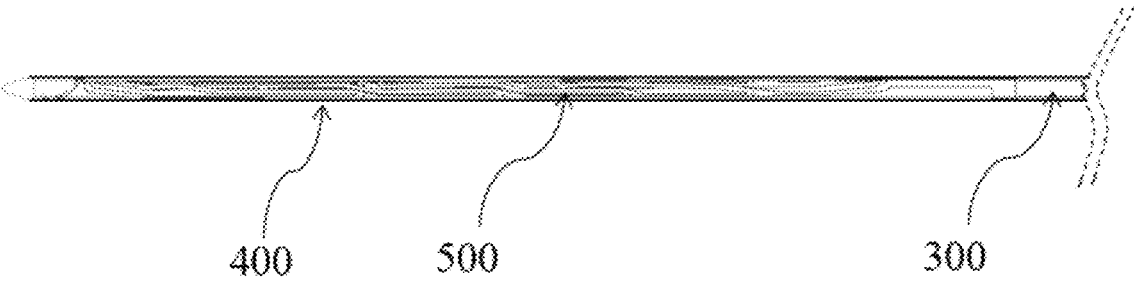
FIG. 12 is a structural diagram of the embolic protection device of FIG. 9 being housed within a sheath.

The sliding-restraint ring(s) 160 may be arranged on at least one head end 132 of one or more supporting rods 130 of the embolic protection device 500, and the number of the sliding-restraint ring(s) 160 on each head end 132 may be provided as desired. As shown in FIGS. 9 and 10, a sliding-restraint ring 160 is arranged on a head end 132 of a distal-most supporting rod 130 of the embolic protection device 500, which can not only prevent the distal end of the embolic protection device 500 from shifting with respect to the sheath-core 300 which may result in poor sealing, but also facilitate the supporting rod 130 to better support the filter screen 120 by conforming the sheath-core 300 to the curvature of the arch of the aorta 200, enabling a tighter attachment and a full filtration of the filter screen 130 at the three branches 210, and further preventing the head end 132 of the supporting rod 130 from puncturing the filter screen 120 or the inner wall of the arch of the aorta 200. In other implementations and as shown in FIG. 11, the sliding-restraint ring(s) 160 may be arranged at the distal end portion or the proximal end portion of the frame 110 of the embolic protection device 500. In other implementations, at least one sliding-restraint ring 160 can be arranged on the distal end portion of the frame 110 of the embolic protection device 500 and at least one head end 132 of at least one supporting rod 130, separately. As shown in FIG. 12, the proximal end of the embolic protection device 500 is fixed to the distal end of the sheath-core 300, the distal end is relatively fixed to the sheath-core 300 through the sliding-restraint ring 160 on the frame 110, and the embolic protection device 500 and the distal end of the sheath-core 300 are both housed in the distal end of the sheath 400, thus assuming a compressed state. The embolic protection device 100 of Embodiment 1 is housed in the sheath 400 in a manner similar to that of FIG. 12.

Figure 13:
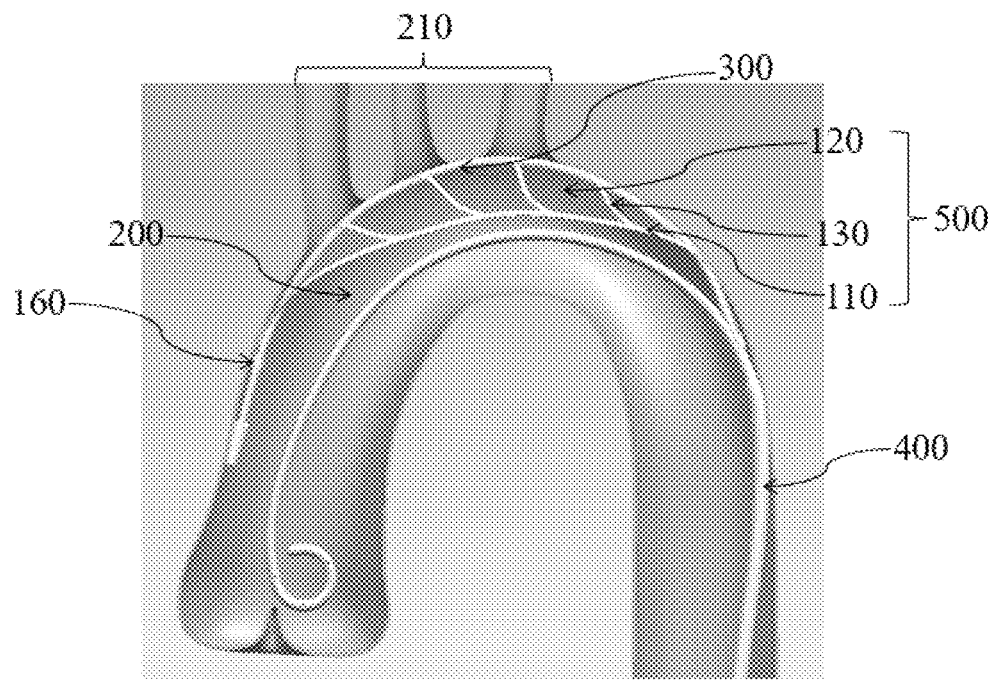
FIG. 13 is a schematic diagram of the embolic protection device of FIG. 9 being implanted at an arch of the aorta.

Prior to a surgery, one end of the embolic protection device 500 needs to be fixed in place on the distal end of the sheath-core 300. The proximal end of the embolic protection device 500 can be fixed on the sheath-core 300 while the distal end can be relatively fixed by passing through the distal end of the sheath-core 300 through the arranged sliding-restraint ring 160. Alternatively, the distal end of the embolic protection device 500 can be fixed on the sheath-core 300 while the proximal end can be relatively fixed by passing through the distal end of the sheath-core 300 through the arranged sliding-restraint ring 160. In FIG. 13, for example, the proximal end portion of the embolic protection device 500 is fixed to the distal end of the sheath-core 300, and the distal end is relatively fixed by passing through the distal end of the sheath-core 300 through the sliding-restraint ring 160 located on the frame 110. The surgical procedure is generally the same as that of Embodiment 1, which will not be described in detail herein.

The sliding-restraint ring 160 on the embolic protection device 500 allows the embolic protection device 500 to slide along the axial direction of the sheath-core 300 throughout release, deployment, and retrieval processes to conform well to the curved configuration of the arch of the aorta 200 to further reduce the risk of twisting or over-deflection of the embolic protection device 500.

Embodiment 3

Referring to FIGS. 14-21, another embolic protection device and an embolic protection system thereof are provided in Embodiment 3. The embolic protection device 600 of Embodiment 3 is generally similar to the embolic protection device 100 of Embodiment 1, as are the surgical procedures. The main difference between the two devices lies in that the distal section 142 of the connecting member 140 of the embolic protection device 600 of Embodiment 3 is rotatably connected to the proximal end of the frame 110. In the embolic protection system of Embodiment 3, after the distal end of the sheath-core enters the proximal end of the proximal section 141 of the connecting member 140 and leaves the distal end, the sheath-core extends towards the distal end for a further distance, until the distal end portion of the sheath-core is closer to the distal end than the distal end portion of the embolic protection device 600.

The embolic protection device 600 may be fixed to the arch of the aorta to prevent thrombi from entering cerebral vessels so as to prevent conditions such as stroke. The embolic protection device 600 is joined to the sheath-core and can be pushed out from or retrieved into the sheath by pushing and drawing the sheath-core. When the embolic protection device 600 is released at the arch of the aorta, it often occurs that the embolic protection device 600 cannot be fully deployed due to the compression and friction of the vessel wall, resulting in flexing of the frame 110, which may lead to the risk that the embolic protection device 600 cannot cover the cerebral vessels and affect the performance of the device. In the embodiment of the present invention, the distal section 142 of the connecting member 140 of the embolic protection device 600 is rotatably connected to the proximal end of the frame 110, such that the connecting member 140 of the embolic protection device 600 has good deformability, so as to provide clearance for the embolic protection device 600 for full deployment when the embolic protection device 600 is compressed after release, thereby avoiding flexing of the frame 110.

Figure 14:
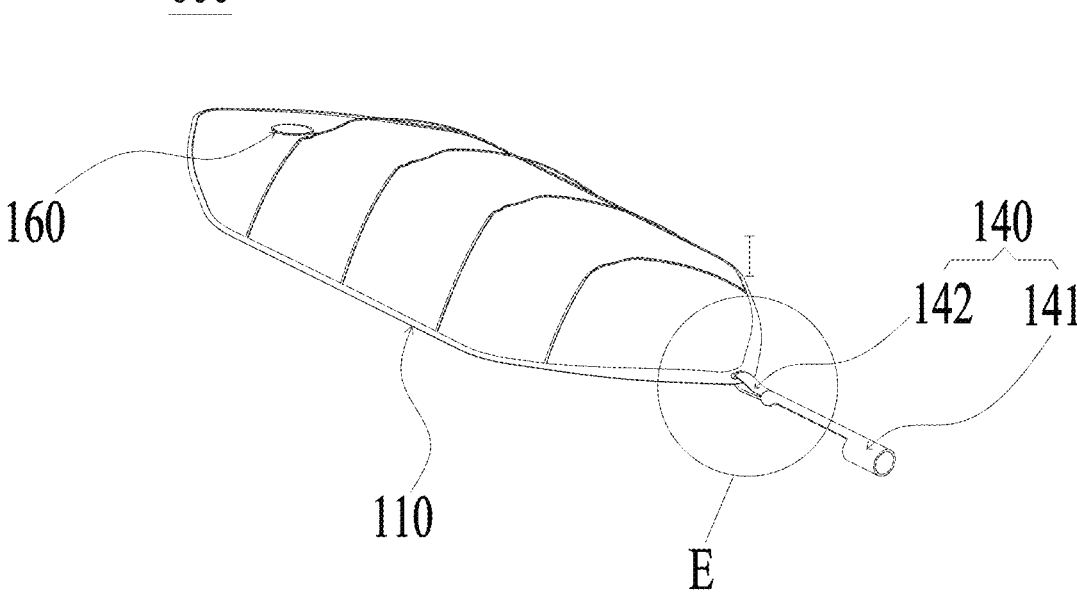
FIG. 14 is an overall structural diagram of an embolic protection device of Embodiment 3.
Figure 15:
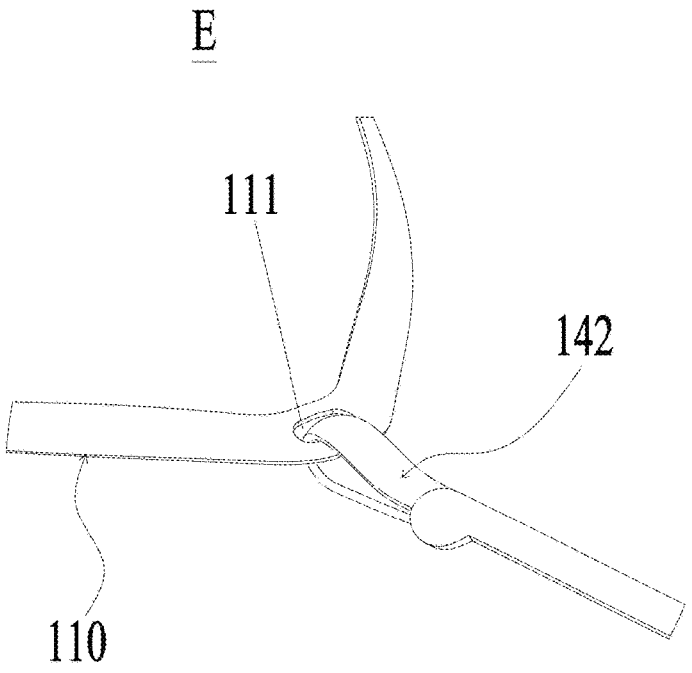
FIG. 15 is an enlarged view of portion E in FIG. 14.

Specifically in the embolic protection device 600 as shown in FIGS. 14 and 15, at least one connecting hole 111 is arranged on the proximal end of the frame 110, and the distal section 142 of the connecting member 140 is fixed to the connecting member 140 through the connecting hole 111, in particular to the distal section 142 itself, such that the connecting member 140 is rotatably connected to the frame 110. The distal section 142 may be fixed by welding, riveting, punching, or gluing after passing through the connecting hole 111, or may be woven and wound around the distal section 142 itself for fixation, which is not limited specifically in the embodiment of the present invention. Further, when the fixation is performed by welding, the distal section 142 may be provided with a welding point having a width greater than that of the distal section 142, and the distal section 142 may be welded at the welding point after passing through the connecting hole 111, thereby increasing the welding area and ensuring the strength of the welding.

Figure 16:
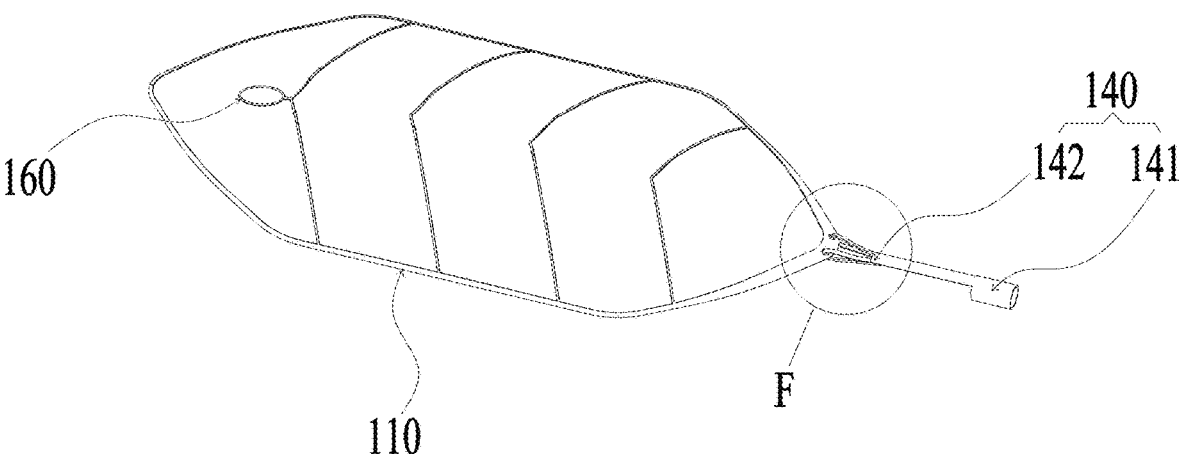
FIG. 16 is another structural diagram of an embolic protection device of Embodiment 3.
Figure 17:
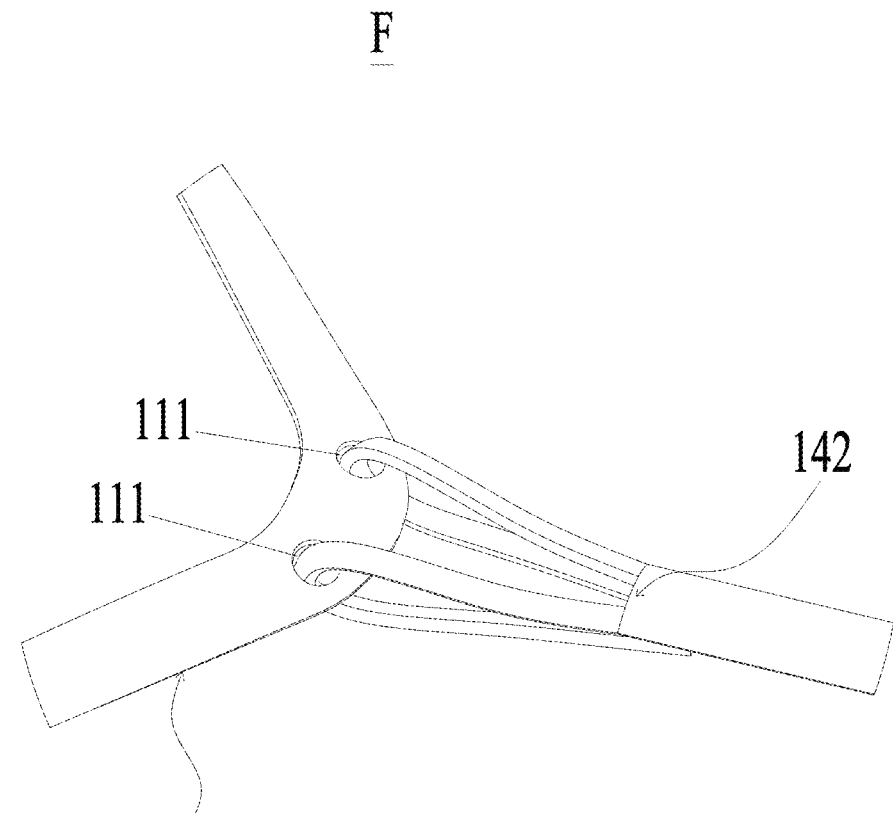
FIG. 17 is an enlarged view of portion F in FIG. 16.
Figure 18:
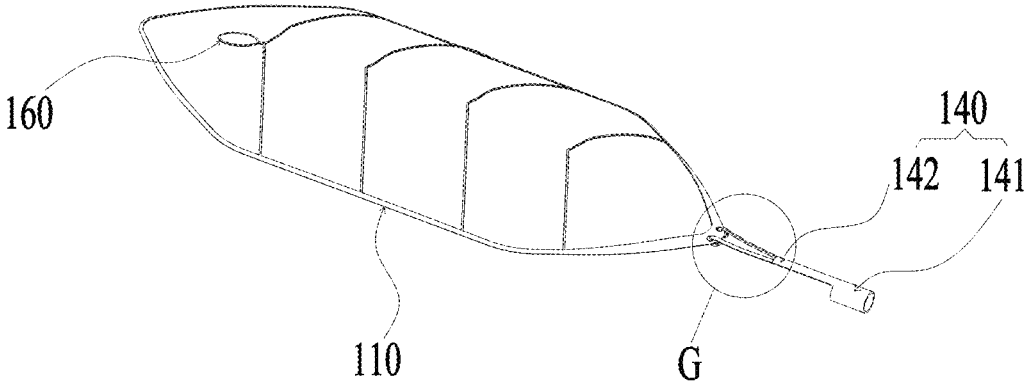
FIG. 18 is yet another structural diagram of an embolic protection device of Embodiment 3.
Figure 19:
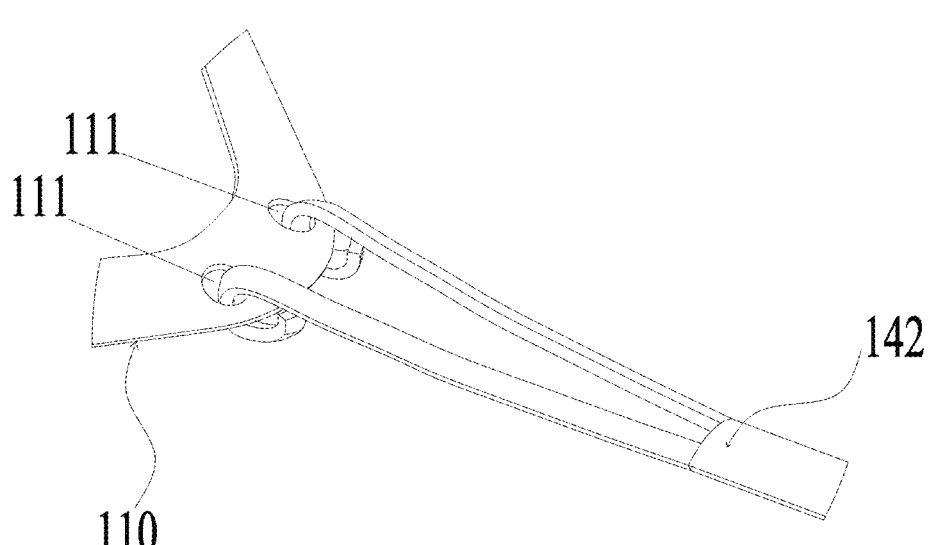
FIG. 19 is an enlarged view of portion G in FIG. 18.
Figure 20:
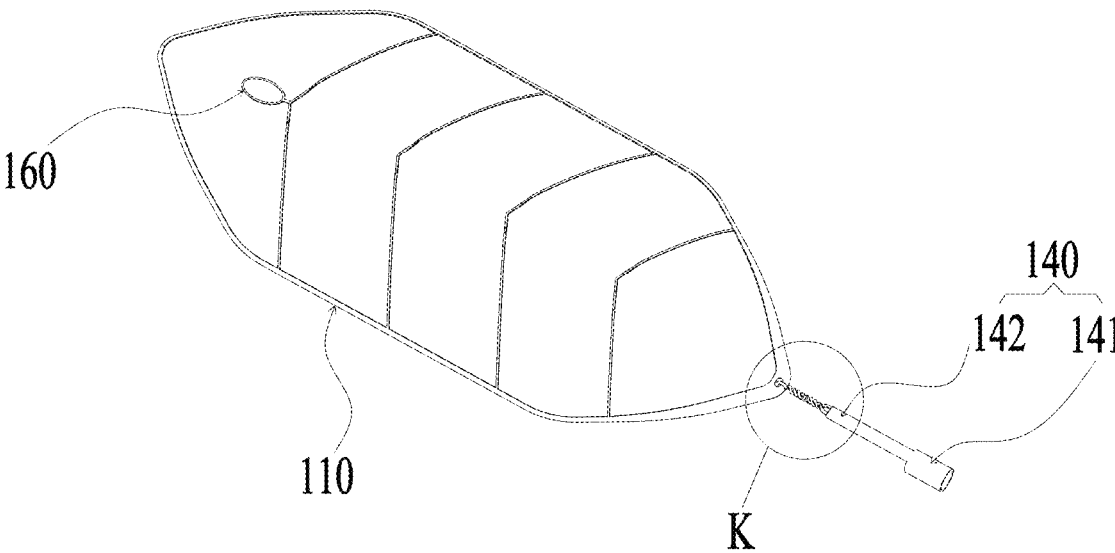
FIG. 20 is still another structural diagram of an embolic protection device of Embodiment 3.
Figure 21:
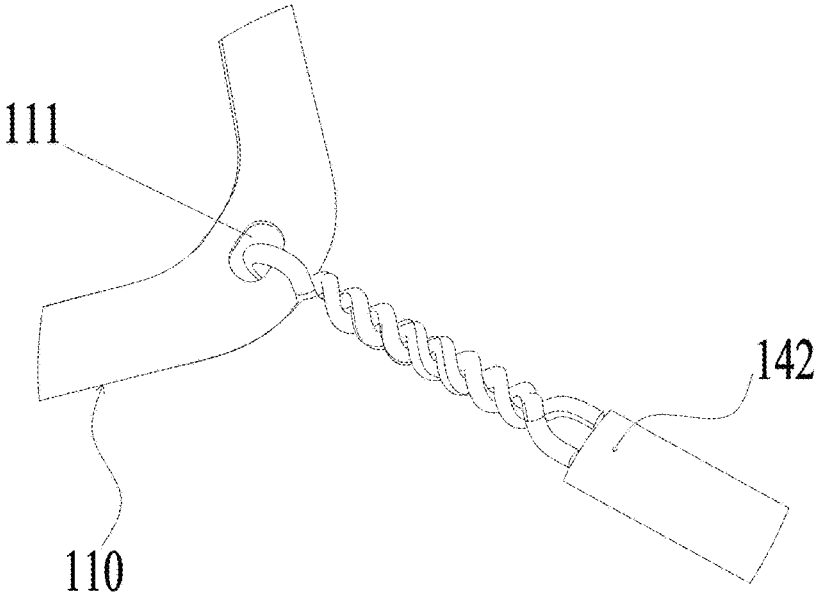
FIG. 21 is an enlarged view of portion K in FIG. 20.

As an alternative and as shown in FIGS. 16 and 17, two connecting holes 111 may be arranged on the proximal end of the frame 110, and the distal section 142 of the connecting member 140 may be cut into two bifurcated sections which are fixed at the junction of the distal section 142 after passing through the two connecting holes 111, separately. As another alternative and as shown in FIGS. 18 and 19, two connecting holes 111 may be arranged on the proximal end of the frame 110, and the distal section 142 of the connecting member 140 may be cut into two bifurcated sections which are fixed to the bifurcated sections themselves after passing through the two connecting holes 111, separately. The diameter of each of the surrounded holes formed by the bifurcated sections passing through the connecting holes 111 is slightly larger than a distance from the each of the connecting holes 111 to the edge of the frame 110 so as to ensure some mobility of the embolic protection device 600. As another alternative and as shown in FIGS. 20 and 21, a connecting hole 111 may be arranged on the proximal end of the frame 110. The distal section 142 of the connecting member 140 passes through the connecting hole 111 and is then woven and wound for a certain length, or a wire of a suitable diameter may pass through the connecting hole 111 and then be woven and wound for a certain length and then welded to the distal section 142 of the connecting member 140. The wire may be a nitinol wire.

Further, as shown in FIG. 14, in the embolic protection system of Embodiment 3, the embolic protection device 600 may be provided with at least one sliding-restraint ring 160 which may be arranged on the frame 110 or on at least one head end 132 of the supporting rods 130, such that when the embolic protection device 600 is compressed by the arch of the aorta, the sliding-restraint ring 160 can move axially along the sheath-core, such that the whole embolic protection device 600 can curve and deform adaptively to be better attached to the upper wall of the arch of the aorta, achieving a greater embolic protection effect, while preventing the embolic protection device 600 from shifting with respect to the sheath-core which may result in ineffective filtration of thrombi, etc. The specific arrangement is described with reference to Embodiment 2, which will not be described in detail in the embodiment of the present invention.

Embodiment 4

Figure 22:
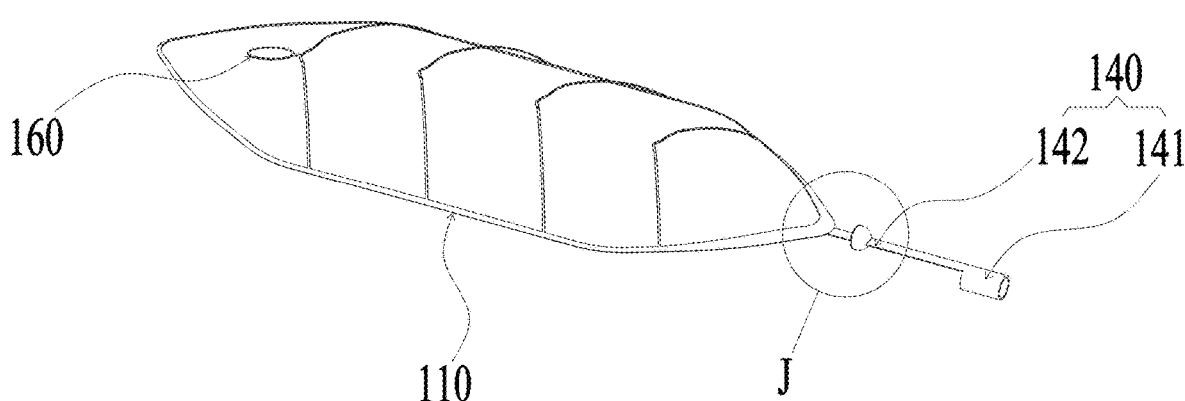
FIG. 22 is an overall structural diagram of an embolic protection device of Embodiment 4.
Figure 23:
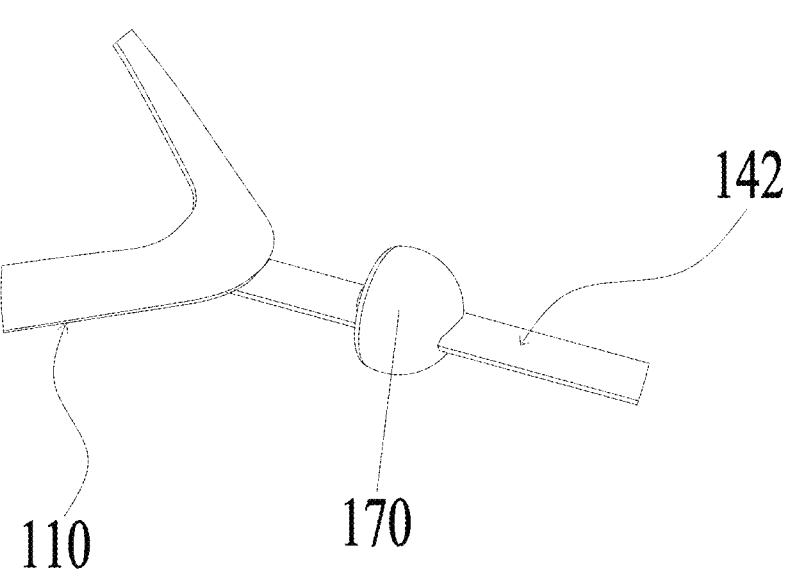
FIG. 23 is an enlarged view of portion J in FIG. 21.
Figure 24:
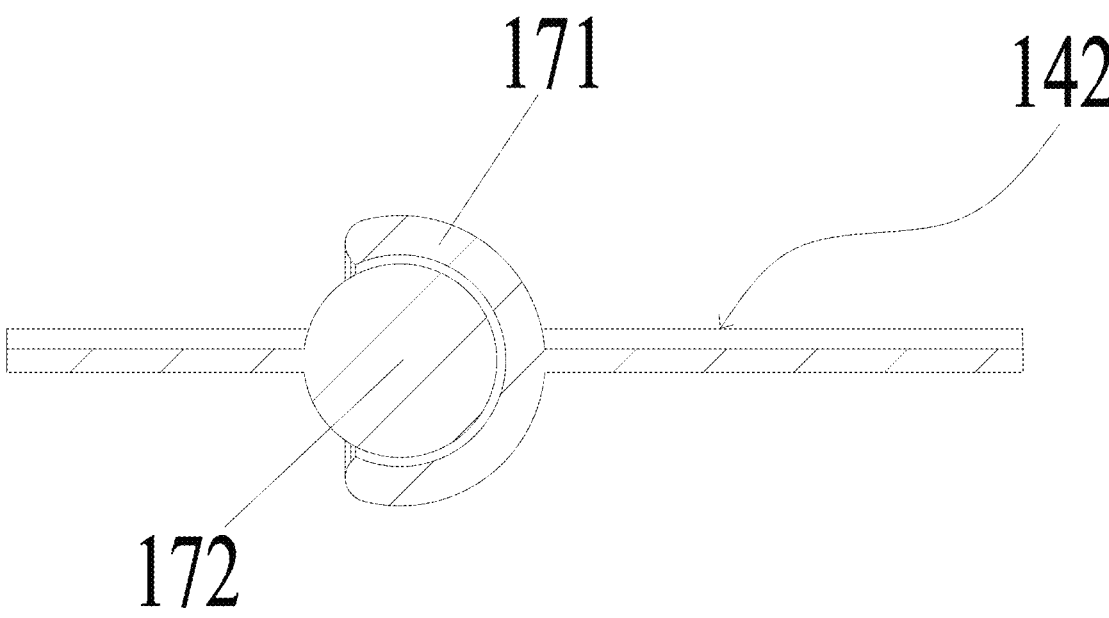
FIG. 24 is a cross-sectional view of a universal ball of an embolic protection device.

Referring to FIGS. 22-24, another embolic protection device and an embolic protection system thereof are provided in Embodiment 4. The embolic protection device 700 of Embodiment 4 is generally similar to the embolic protection device 600 of Embodiment 3 in structure and function, as are the surgical procedures, and the distal section 142 of the connecting member 140 is rotatably connected to the proximal end of the frame 110 as well. The main difference between the two devices lies in that the connecting member 140 of the embolic protection device 700 is connected to the frame 110 by a universal ball 170.

Specifically in the embolic protection device 700, the universal ball 170 includes a ball seat 171 and a rotatable ball 172 disposed in the ball seat 171. The ball seat 171 includes a recess, and the distance from the opening of the recess to the bottom of the recess is greater than the radius of the ball 172 and less than the diameter of the ball 172, such that the ball 172 can rotate freely in the ball seat 171 without disengaging from the ball seat 171.

One of the ball seat 171 and the ball 172 is connected to the distal section 142 of the connecting member 140, and the other is connected to the proximal end of the frame 110. The ball seat 171 or the ball 172 that is connected to the frame 110 may be directly connected to the frame 110 or indirectly connected to the frame 110 via a connecting rod. The connecting rod may be a nitinol rod.

Embodiment 5

Figure 25:
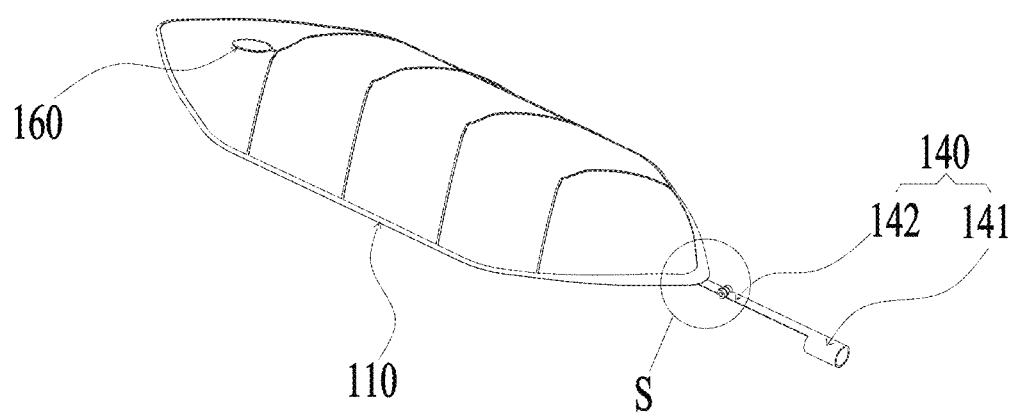
FIG. 25 is an overall structural diagram of an embolic protection device of Embodiment 5.
Figure 26:
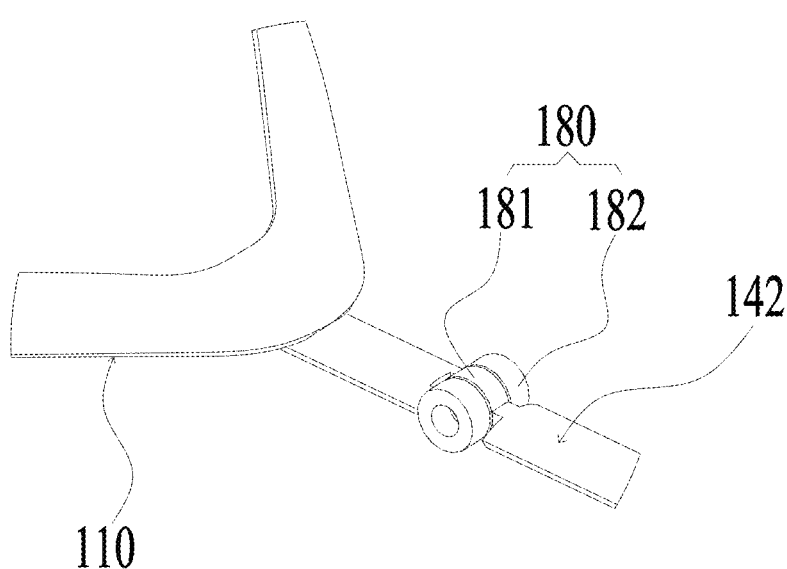
FIG. 26 is an enlarged view of portion S in FIG. 25.

Referring to FIGS. 25 and 26, another embolic protection device and an embolic protection system thereof are provided in Embodiment 5. The embolic protection device 800 of Embodiment 5 is generally similar to the embolic protection device 700 of Embodiment 4 in structure and function, as are the surgical procedures, and the distal section 142 of the connecting member 140 is rotatably connected to the proximal end of the frame 110 as well. The main difference between the two devices lies in that the connecting member 140 of the embolic protection device 800 is connected to the frame 110 by a hinge 180.

Specifically in the embolic protection device 800, the hinge 180 is a rotary shaft structure including a first rotating member 181 and a second rotating member 182 that are coaxially and rotatably connected. One of the first rotating member 181 and the second rotating member 182 is connected to the distal section 142 of the connecting member 140, and the other is connected to the proximal end of the frame 110. The first rotating member 181 or the second rotating member 182 that is connected to the frame 110 may be directly connected to the frame 110 or indirectly connected to the frame 110 via a connecting rod. The connecting rod may be a nitinol rod.

Various technical features of the embodiments above can be arbitrarily combined. In order to make the description concise, not all the possible combinations of the technical features in the embodiments above are described. However, the combinations of these technical features shall be considered as falling with the scope of the description as long as there is no contradiction therein.

The embodiments described above express only a few implementations of the present invention which are described in detail and should not therefore be construed as limiting the scope of the present invention. It is noted that a person of ordinary skill in the art would be able to make several variations and improvements without departing from the concept of the present invention, which fall within the protection scope of the present invention. Therefore, the protection scope of the present invention shall be subject to the appended claims.

14

The invention claimed is:

1. An embolic protection device, comprising a frame and a filter screen covering the frame, wherein the embolic protection device further comprises a plurality of supporting rods that are arranged at intervals in an axial direction thereof,
   each supporting rod of the plurality of supporting rods comprises:
      a first tail end, a second tail end, and at least one head end that faces a distal end, the first tail end and the second tail end are separately connected to two opposite sides of the frame;
      a first line segment is formed between the first tail end and the head end;
      and a second line segment is formed between the second tail end and the head end, the first line segment extends in a direction from the first tail end to the head end and gradually moves away from the frame, and the second line segment extends in a direction from the second tail end to the head end and gradually moves away from the frame, such that the plurality of supporting rods support the filter screen, which covers the plurality of supporting rods, in a direction facing away from the frame; and
   wherein a sliding-restraint ring is provided on the embolic protection device, both the head end of a distal most supporting rod of the plurality of supporting rods and the sliding-restraint ring protrude from the surface where the frame is located and extend in the distal direction;
   wherein a proximal end of the sliding-restraint ring is disposed at the head end of the distal most supporting rod of the plurality of supporting rods, and a distal end of the sliding restraint ring extends in a distal direction;
   and when a sheath-core is inserted into the sliding-restraint ring and the sheath-core moves distally, the head end of the distal most supporting rod of the plurality of supporting rods is driven to extend distally.

2. The embolic protection device of claim 1, wherein a vertical distance from a highest point on the supporting rods to a horizontal plane is greater than or equal to 0 mm and less than or equal to 30 mm when the embolic protection device is placed on the horizontal plane.

3. The embolic protection device of claim 2, wherein the vertical distance between a vertical projection point of the at least one head end to the horizontal plane and a line connecting vertical projection points of the first tail end and the second tail end to the horizontal plane is greater than or equal to 20 mm and less than or equal to 120 mm.

4. The embolic protection device of claim 3, wherein the shortest distance between the first tail end and the second tail end ranges from 20 mm to 100 mm.

5. The embolic protection device of claim 1, wherein at least one of the head ends curves and extends towards the distal end and towards the frame.

6. The embolic protection device of claim 1, wherein at least one of the head ends is provided with a damage-prevention element.

7. The embolic protection device of claim 1, wherein the embolic protection device is provided with at least one imaging member at a proximal and/or distal end thereof.

8. The embolic protection device of claim 1, further comprising a connecting member connected to a proximal end of the frame.

9. The embolic protection device of claim 8, wherein the connecting member is rotatably connected to the frame.

10. The embolic protection device of claim 9, wherein at least one connecting hole is arranged on the proximal end of the frame, and a distal end of the connecting member is fixed to the connecting member through the connecting hole, such that the connecting member is rotatably connected to the frame.

11. The embolic protection device of claim 9, wherein the connecting member is connected to the frame by a universal ball.

12. The embolic protection device of claim 9, wherein the connecting member is connected to the frame by a hinge.

13. An embolic protection system, comprising an elongate sheath-core and the embolic protection device of claim 1.

14. The embolic protection system of claim 13, wherein at least one sliding-restraint ring is provided on the embolic protection device, one end of the embolic protection device is fixed to the sheath-core and the other end is axially movable along the sheath-core through the sliding-restraint ring.

15. The embolic protection device of claim 5, wherein at least one of the head ends is provided with a damage-prevention element.

* * * * *